(12) United States Patent
Haverkost et al.

(10) Patent No.: US 7,828,833 B2
(45) Date of Patent: Nov. 9, 2010

(54) COMPOSITE EPTFE/TEXTILE PROSTHESIS

(75) Inventors: Pat Haverkost, Brooklyn Center, MN (US); Paul Chouinard, Maple Grove, MN (US); Ronald Rakos, Neshanic Station, NJ (US); Krzysztof Sowinski, Wallington, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/166,842

(22) Filed: Jun. 11, 2002

(65) Prior Publication Data

US 2003/0139806 A1 Jul. 24, 2003

Related U.S. Application Data

(60) Provisional application No. 60/297,401, filed on Jun. 11, 2001.

(51) Int. Cl.
*A61F 2/06* (2006.01)

(52) U.S. Cl. .................... 623/1.13; 623/1.15

(58) Field of Classification Search ............. 623/1.1, 623/1.13, 1.15, 1.39, 1.44
See application file for complete search history.

(56) References Cited

U.S. PATENT DOCUMENTS

| | | | |
|---|---|---|---|
| 4,850,999 A * | 7/1989 | Planck | 623/1.44 |
| 4,925,710 A | 5/1990 | Buck et al. | |
| 4,955,899 A | 9/1990 | Della Corna et al. | |
| 5,026,591 A | 6/1991 | Henn et al. | |
| 5,123,917 A | 6/1992 | Lee | |
| 5,133,742 A | 7/1992 | Pinchuk | |
| 5,282,824 A | 2/1994 | Gianturco | |
| 5,389,106 A | 2/1995 | Tower | |
| 5,466,509 A | 11/1995 | Kowligi et al. | |
| 5,507,771 A | 4/1996 | Gianturco | |
| 5,562,697 A | 10/1996 | Christiansen | |
| 5,562,728 A | 10/1996 | Lazarus et al. | |
| 5,591,195 A | 1/1997 | Taheri et al. | |
| 5,620,763 A | 4/1997 | House et al. | |
| 5,628,788 A * | 5/1997 | Pinchuk | 623/1.2 |
| 5,653,697 A | 8/1997 | Quiachon et al. | |
| 5,674,241 A | 10/1997 | Bley et al. | |
| 5,700,285 A | 12/1997 | Myers et al. | |
| 5,713,917 A | 2/1998 | Leonhardt et al. | |
| 5,718,973 A | 2/1998 | Lewis et al. | |
| 5,735,892 A | 4/1998 | Myers et al. | |
| 5,749,880 A * | 5/1998 | Banas et al. | 606/198 |
| 5,799,384 A | 9/1998 | Schwartz et al. | |

(Continued)

FOREIGN PATENT DOCUMENTS

JP  0 351 584  *  6/1989

(Continued)

*Primary Examiner*—Corrine M McDermott
*Assistant Examiner*—Christopher D Prone
(74) *Attorney, Agent, or Firm*—Vidas, Arrett & Steinkraus, P.A.

(57) ABSTRACT

A composite intraluminal prosthesis which is preferably used as a vascular prosthesis includes a layer of ePTFE and a layer of textile material which are secured together by an elastomeric bonding agent. The ePTFE layer includes a porous microstructure defined by nodes interconnected by fibrils. The adhesive bonding agent is preferably applied in solution so that the bonding agent enters the pores of the microstructure of the ePTFE. This helps secure the textile layer to the ePTFE layer.

15 Claims, 3 Drawing Sheets

U.S. PATENT DOCUMENTS

| | | | |
|---|---|---|---|
| 5,800,510 A * | 9/1998 | Schmitt | 623/23.72 |
| 5,810,870 A | 9/1998 | Myer et al. | |
| 5,824,042 A | 10/1998 | Lombardi et al. | |
| 5,836,926 A | 11/1998 | Peterson et al. | |
| 5,843,158 A | 12/1998 | Lenker et al. | |
| 5,843,161 A | 12/1998 | Solovay | |
| 5,925,074 A | 7/1999 | Gingras et al. | |
| 5,925,075 A | 7/1999 | Myers et al. | |
| 5,957,974 A | 9/1999 | Thompson et al. | |
| 5,961,546 A | 10/1999 | Robinson et al. | |
| 5,968,091 A * | 10/1999 | Pinchuk et al. | 623/1.16 |
| 6,019,778 A | 2/2000 | Wilson et al. | |
| 6,042,578 A | 3/2000 | Dihn et al. | |
| 6,080,198 A | 6/2000 | Lentz et al. | |
| 6,099,557 A | 8/2000 | Schmitt | |
| 6,120,539 A | 9/2000 | Eldridge et al. | |
| 6,124,523 A | 9/2000 | Banas et al. | |
| 6,136,022 A | 10/2000 | Nunez et al. | |
| 6,159,239 A | 12/2000 | Greenhalgh | |
| 6,264,684 B1 * | 7/2001 | Banas et al. | 623/1.13 |
| 6,344,052 B1 | 2/2002 | Greenan et al. | |
| 6,375,787 B1 | 4/2002 | Lukic | |
| 7,510,571 B2 | 3/2009 | Spiridigliozzi et al. | |
| 7,560,006 B2 | 7/2009 | Rakos et al. | |
| 2005/0283224 A1 | 12/2005 | King | |
| 2006/0020328 A1 | 1/2006 | Tan | |
| 2006/0058867 A1 | 3/2006 | Thistle et al. | |
| 2006/0264138 A1 | 11/2006 | Sowinski et al. | |

FOREIGN PATENT DOCUMENTS

| | | |
|---|---|---|
| WO | WO 02/43621 | 6/2002 |
| WO | WO 02/100454 | 12/2002 |

* cited by examiner

COMPOSITE EPTFE/TEXTILE PROSTHESIS

CROSS-REFERENCE TO RELATED APPLICATION

The present application claims priority to U.S. Provisional Application No. 60/297,401-Jul. 11, 2001. The present application is being concurrently filed with 10/167,676, claiming priority to the same application, and herein incorporated by reference.

FIELD OF THE INVENTION

The present invention relates generally to an implantable prosthesis. More particularly, the present invention relates to a composite multilayer implantable structure having a textile layer, an expanded polytetrafluoroethylene layer (ePTFE) and an elastomeric bonding agent layer within the ePTFE porous layer, which joins the textile and ePTFE layer to form an integral structure.

BACKGROUND OF THE INVENTION

Implantable prostheses are commonly used in medical applications. One of the more common prosthetic structures include tubular prostheses which may be used as vascular grafts to replace or repair damaged or diseased blood vessels. To maximize the effectiveness of such a prosthesis, it should be designed with characteristics which closely resemble that of the natural body lumen which it is repairing or replacing.

One form of a conventional tubular prosthesis specifically used for vascular grafts includes a textile tubular structure formed by weaving, knitting or braiding synthetic fibers into a tubular configuration. Tubular textile structures have the advantage of being naturally porous which allows desired tissue ingrowth and assimilation into the body. This porosity, which allows for ingrowth of surrounding tissue, must be balanced with fluid tightness so as to minimize leakage during the initial implantation stage.

Attempts to control the porosity of the graft while providing a sufficient fluid barrier have focused on increasing the thickness of the textile structure, providing a tighter stitch construction and including features such as velours to the graft structure. Further most textile grafts require the application of a biodegradable natural coating, such as collagen or gelatin in order to render the graft blood tight. While grafts formed in this manner overcome certain disadvantages inherent in attempts to balance porosity and fluid tightness, these textile prostheses may exhibit certain undesirable characteristics. These characteristics may include an undesirable increase in the thickness of the tubular structure, which makes implantation more difficult. These textile tubes may also be subject to kinking, bending, twisting or collapsing during handling. Moreover, application of a coating may render the grafts less desirable to handle from a tactility point of view.

It is also well known to form a prosthesis, especially a tubular graft, from polymers such as polytetrafluoroethylene (PTFE). A tubular graft may be formed by stretching and expanding PTFE into a structure referred to as expanded polytetrafluoroethylene (ePTFE). Tubes formed of ePTFE exhibit certain beneficial properties as compared with textile prostheses. The expanded PTFE tube has a unique structure defined by nodes interconnected by fibrils. The node and fibril structure defines micropores which facilitate a desired degree of tissue ingrowth while remaining substantially fluid-tight. Tubes of ePTFE may be formed to be exceptionally thin and yet exhibit the requisite strength necessary to serve in the repair or replacement of a body lumen. The thinness of the ePTFE tube facilitates ease of implantation and deployment with minimal adverse impact on the body.

One particular advantage of using ePTFE vascular grafts derives from its thinness. ePTFE vascular grafts possess a low profile because of its ultra-thin characteristics. This is particularly advantageous for implantable prostheses which are often delivered to the implantation site through blood vessels which are tortuous and narrow. The low profile facilitates delivery.

While exhibiting certain superior attributes, ePTFE tubes are not without certain disadvantages. Grafts formed of ePTFE tend to be relatively non-compliant as compared with textile grafts and natural vessels. Further, while exhibiting a high degree of tensile strength, ePTFE grafts are susceptible to tearing. Additionally, PTFE grafts lack the suture compliance of coated textile grafts. This may cause undesirable bleeding at the suture hole. Thus, the ePTFE grafts lack many of the advantageous properties of certain textile grafts.

It is also known that it is extremely difficult to join PTFE and ePTFE to other materials via adhesives or bonding agents due to its natural hydrophobic character. Wetting of the surface by the adhesive is necessary to achieve adhesive bonding, and PTFE and ePTFE are extremely difficult to wet without destroying the chemical properties of the polymer. Thus, heretofore, attempts to bond ePTFE to other dissimilar materials such as textiles, has been difficult.

It is also known to use vascular grafts in conjunction with support structures. Such support structures typically come in the form of stents, which are formed of metal or polymeric materials generally formed in a tubular structure and are used to hold a vein or artery open. Stents are well known in the art and may be self-expanding or radially expandable by balloon expansion. Examples of stent/graft configurations known in the art can be seen in U.S. Pat. Nos. 5,700,285; 5,749,880; and 5,123,917, each of which are herein incorporated by reference. It is advantageous to use stent/graft configurations because the stent provides and ensures the patency of the prosthesis, while the vascular graft provides biocompatible properties in a vessel more suitable for blood to flow through.

It is apparent that conventional textile prostheses as well as ePTFE prostheses have acknowledged advantages and disadvantages. Neither of the conventional prosthetic materials exhibits fully all of the benefits desirable for use as a vascular prosthesis.

It is therefore desirable to provide an implantable prosthesis, preferably in the form of a tubular vascular prosthesis, which achieves many of the above-stated benefits without the resultant disadvantages associated therewith. It is also desirable to provide an implantable multi-layered patch which also achieves the above-stated benefits without the disadvantages of similar conventional products.

It is also desirable to provide a prosthesis with the advantages of both textile and ePTFE artificial grafts, as well as the advantages of the graft being used in conjunction with a stent structure.

SUMMARY OF THE INVENTION

The present invention provides a composite multi-layered implantable prosthetic structure which may be used in various applications, especially vascular applications. The implantable structure of the present invention may include an ePTFE-lined textile graft, an ePTFE graft, covered with a textile covering, or a vascular patch including a textile surface and an opposed ePTFE surface. Moreover, additional ePTFE layers may be combined with any of these embodiments.

The composite multi-layered implantable structure of the present invention includes a first layer formed of a textile material and a second layer formed of expanded polytetrafluoroethylene (ePTFE) having a porous microstructure defined by nodes interconnected by fibrils. An elastomeric bonding agent is applied to the second layer and disposed within the pores of the microstructure for securing the first layer to the second layer.

In another embodiment, the composite multi-layered implantable structure of the present invention may have a first inner tubular layer and a second outer tubular layer, both formed of ePTFE having a porous microstructure defined by nodes interconnected by fibrils. The first and second layers of ePTFE also preferably have a support structure positioned therebetween. Typically, this support structure takes the form of a radially expandable member, preferably a stent. A third tubular layer formed of textile material is circumferentially disposed exteriorly to the first and second layers, and an elastomeric bonding agent is applied to the second layer of ePTFE or the textile layer, and disposed within the pores of the ePTFE microstructure when the layers are bonded together. The bonding agent helps secure the second outer layer of ePTFE to the third textile layer.

In a preferred embodiment, the multi-layered implantable structure further comprises a fourth layer of textile material circumferentially disposed interior to said first and second ePTFE layer and bonded to the first ePTFE layer with the elastomeric bonding agent. It is contemplated to further secure additional layers either interior or exterior said composite structure.

The bonding agent may be selected from a group of materials including biocompatible elastomeric materials such as urethanes, silicones, isobutylene/styrene copolymers, block polymers, and combinations thereof.

The tubular composite grafts of the present invention may also be formed from appropriately layered sheets which can then be overlapped to form tubular structures. Bifurcated, tapered conical and stepped-diameter tubular structures may also be formed from the present invention.

The textile layer may be formed of various textile structures including knits, weaves, stretch knits, braids, any nonwoven processing techniques, and combinations thereof. Various biocompatible polymeric materials may be used to form the textile structures, including polyethylene terephthalate (PET), naphthalene dicarboxylate derivatives such as polyethylene naphthalate, polybutylene naphthalate, polytrimethylene naphthalate, trimethylenediol naphthalate, ePTFE, natural silk, polyethylene and polypropylene, among others. PET is a particularly desirable material for forming the textile layer.

The bonding agent is applied in solution to one surface of the ePTFE layer, preferably by spray coating. The textile layer is then placed in contact with the coated surface of the ePTFE layer. The bonding agent may also be applied in powder form by any known techniques; e.g. electrostatic spray. The bonding agent may also be applied and activated by thermal and/or chemical processes well known in the art.

The present invention also provides an ePTFE-lined textile graft. The lined textile graft includes a tubular textile substrate bonded using a biocompatible elastomeric material to a tubular liner of ePTFE. A coating of an elastomeric bonding agent may be applied to the surface of the ePTFE liner so that the bonding agent is present in the micropores thereof. The coated liner is then secured to the tubular textile structure via the elastomeric bonding agent. The liner and textile graft can each be made very thin and still maintain the advantages of both types of materials.

The present invention further provides a textile-covered ePTFE graft. The tubular ePTFE graft structure includes micropores defined by nodes interconnected by fibrils. A coating of an elastomeric bonding agent is applied to the surface of the ePTFE tubular structure with the bonding agent being resident within the microporous structure thereof. A tubular textile structure is applied to the coated surface of the ePTFE tubular structure and secured thereto by the elastomeric bonding agent.

Additionally, the present invention provides an implantable patch which may be used to cover an incision made in a blood vessel, or otherwise support or repair a soft tissue body part, such as a vascular wall. The patch of the present invention includes an elongate ePTFE substrate having one surface positioned against the exterior vascular wall. The opposed surface is coated with a bonding agent, such that the bonding agent resides within the microporous structure of the ePTFE substrate. A planar textile substrate is positioned over the coated surface of the ePTFE substrate so as to form a composite multi-layered implantable structure.

The composite multi-layered implantable structures of the present invention are designed to take advantage of the inherent beneficial properties of the materials forming each of the layers. The textile layer provides for enhanced tissue ingrowth, high suture retention strength and longitudinal compliance for ease of implantation. The ePTFE layer provides the beneficial properties of sealing the textile layer without need for coating the textile layer with a sealant such as collagen. The sealing properties of the ePTFE layer allow the wall thickness of the textile layer to be minimized. Further, the ePTFE layer exhibits enhanced thrombo-resistance upon implantation. Moreover, the elastomeric bonding agent not only provides for an integral composite structure, but adds further puncture-sealing characteristics to the final prosthesis.

In further aspects of the invention, the implantable structure may be used in conjunction with radially-expandable members such as stents and other structures which are capable of maintaining patency of the implantable structure in a bodily vessel. For example, a stent may be disposed between two ePTFE layers with the outer ePTFE layer being joined to the tubular textile structure via the elastomeric bonding agent. Optionally, a textile reinforcement may be secured to the inner ePTFE layer via the elastomeric bonding agent, in addition to the outer tubular textile structure. Any stent construction known to those skilled in the art may be used, including self-expanding stents, as well as, balloon-expandable stents.

Various additives such as drugs, growth-factors, anti-thrombogenic agents and the like may also be employed.

DETAILED DESCRIPTION OF THE PREFERRED EMBODIMENT

The present invention provides a composite implantable prosthesis, desirably a vascular prosthesis including two layers of ePTFE surrounding a stent, and a layer of a textile material. The ePTFE stent/graft layers are secured together, with the textile layer, by an elastomeric bonding agent. The vascular prosthesis of the present invention may include a ePTFE-lined textile vascular graft, an ePTFE vascular graft including a textile covering and a composite ePTFE/textile vascular patch.

Figure 1:
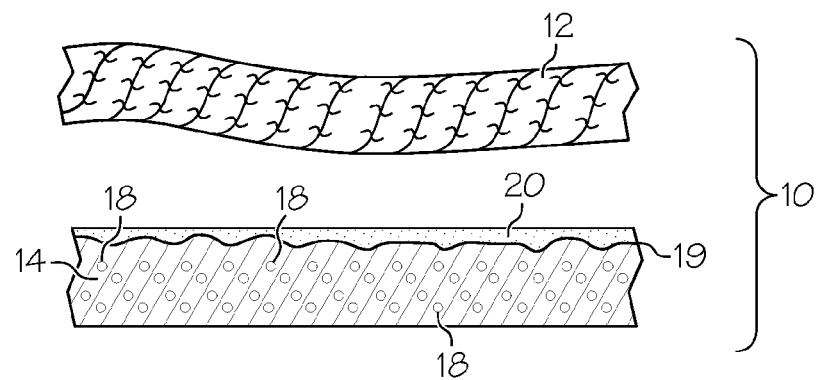
FIG. 1 shows a schematic cross-section, a portion of a composite multi-layered implantable structure of the present invention.

Referring to FIG. 1, a schematic cross-section of a portion of a representative vascular prosthesis 10 is shown. As noted above, the prosthesis 10 may be a portion of a graft, patch or any other implantable structure.

The prosthesis 10 includes a first layer 12 which is formed of a textile material. The textile material 12 of the present invention may be formed from synthetic yarns that may be flat, shaped, twisted, textured, pre-shrunk or un-shrunk. Preferably, the yarns are made from thermoplastic materials including, but not limited to, polyesters, polypropylenes, polyethylenes, polyurethanes, polynaphthalenes, polytetrafluoroethylenes and the like. The yarns may be of the multifilament, monofilament or spun types. In most vascular applications, multifilaments are preferred due to the increase in flexibility. Where enhanced crush resistance is desired, the use of monofilaments have been found to be effective. As is well known, the type and denier of the yarn chosen are selected in a manner which forms a pliable soft tissue prosthesis and, more particularly, a vascular structure have desirable properties.

The prosthesis 10 further includes a second layer 14 formed of expanded polytetrafluoroethylene (ePTFE). The ePTFE layer 14 may be produced from the expansion of PTFE formed in a paste extrusion process. The PTFE extrusion may be expanded and sintered in a manner well known in the art to form ePTFE having a microporous structure defined by nodes interconnected by elongate fibrils. The distance between the nodes, referred to as the internodal distance (IND), may be varied by the parameters employed during the expansion and sintering process. The resulting process of expansion and sintering yields pores 18 within the structure of the ePTFE layer. The size of the pores are defined by the IND of the ePTFE layer.

The ePTFE of the present invention may also be "ultrathin" ePTFE as described in commonly-owned applications, U.S. Ser. Nos. 10/012,825 and 10/012,919, the disclosures of which are herein incorporated by reference.

One aspect of the present invention is directed to a green fluoropolymer tube which has a wall thickness of about 250 μm or less, preferably about 200 μm or less, and more preferably about 125 μm or less. With such thinness, the green tube may be formed into a tube of expanded fluoropolymer having a wall thickness of about 250 μm or less, preferably about 200 μm or less, and more preferably about 125 μm or less. Such an expanded fluoropolymer tube is particularly well-suited for use as an endovascular prosthesis, such as a graft, or in a stent-graft, because of its flexibility and strength.

The composite prosthesis 10 of the present invention further includes a bonding agent 20 applied to one surface 19 of ePTFE layer 18. The bonding agent 20 is preferably applied in solution by a spray coating process. However, other processes may be employed to apply the bonding agent.

In the present invention, the bonding agent may include various biocompatible, elastomeric bonding agents such as urethanes, styrene/isobutylene/styrene block copolymers (SIBS), silicones, and combinations thereof. Other similar materials are contemplated. Most desirably, the bonding agent may include polycarbonate urethanes sold under the trade name CORETHANE® by Boston Scientific Corporation, Natick, Mass. This urethane is provided as an adhesive solution with preferably 7.5% Corethane, 2.5 W30, in dimethylacetamide (DMAc) solvent.

The term "elastomeric" as used herein refers to a substance having the characteristic that it tends to resume an original shape after any deformation thereto, such as stretching, expanding, or compression. It also refers to a substance which has a non-rigid structure, or flexible characteristics in that it is not brittle, but rather has compliant characteristics contributing to its non-rigid nature.

The polycarbonate urethane polymers particularly useful in the present invention are more fully described in U.S. Pat. Nos. 5,133,742 and 5,229,431 which are incorporated in their entirety herein by reference. These polymers are particularly resistant to degradation in the body over time and exhibit exceptional resistance to cracking in vivo. These polymers are segmented polyurethanes which employ a combination of hard and soft segments to achieve their durability, biostability, flexibility and elastomeric properties.

The polycarbonate urethanes useful in the present invention are prepared from the reaction of an aliphatic or aromatic polycarbonate macroglycol and a diisocyanate in the presence of a chain extender. Aliphatic polycarbonate macroglycols such as polyhexane carbonate macroglycols and aromatic diisocyanates such as methylene diisocyanate are most desired due to the increased biostability, higher intramolecular bond strength, better heat stability and flex fatigue life, as compared to other materials.

The polycarbonate urethanes particularly useful in the present invention are the reaction products of a macroglycol, a diisocyanate and a chain extender.

A polycarbonate component is characterized by repeating

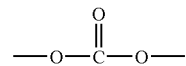

units, and a general formula for a polycarbonate macroglycol is as follows:

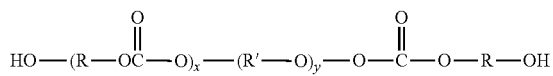

wherein x is from 2 to 35, y is 0, 1 or 2, R either is cycloaliphatic, aromatic or aliphatic having from about 4 to about 40 carbon atoms or is alkoxy having from about 2 to about 20 carbon atoms, and wherein R' has from about 2 to about 4 linear carbon atoms with or without additional pendant carbon groups.

Examples of typical aromatic polycarbonate macroglycols include those derived from phosgene and bisphenol A or by ester exchange between bisphenol A and diphenyl carbonate such as (4,4'-dihydroxy-diphenyl-2,2'-propane) shown below, wherein n is between about 1 and about 12.

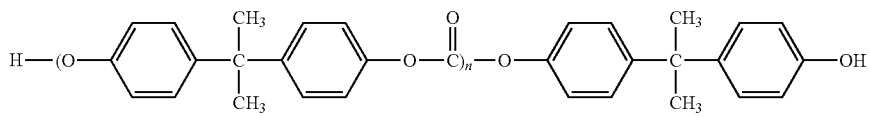

Typical aliphatic polycarbonates are formed by reacting cycloaliphatic or aliphatic diols with alkylene carbonates as shown by the general reaction below:

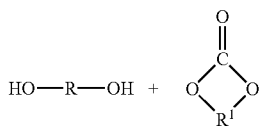

wherein R is cyclic or linear and has between about 1 and about 40 carbon atoms and wherein R1 is linear and has between about 1 and about 4 carbon atoms.

Typical examples of aliphatic polycarbonate diols include the reaction products of 1,6-hexanediol with ethylene carbonate, 1,4-butanediol with propylene carbonate, 1,5-pentanediol with ethylene carbonate, cyclohexanedimethanol with ethylene carbonate and the like and mixtures of above such as diethyleneglycol and cyclohexanedimethanol with ethylene carbonate.

When desired, polycarbonates such as these can be copolymerized with components such as hindered polyesters, for example phthalic acid, in order to form carbonate/ester copolymer macroglycols. Copolymers formed in this manner can be entirely aliphatic, entirely aromatic, or mixed aliphatic and aromatic. The polycarbonate macroglycols typically have a molecular weight of between about 200 and about 4000 Daltons.

Diisocyanate reactants according to this invention have the general structure OCN—R'—NCO, wherein R' is a hydrocarbon that may include aromatic or nonaromatic structures, including aliphatic and cycloaliphatic structures. Exemplary isocyanates include the preferred methylene diisocyanate (MDI), or 4,4-methylene bisphenyl isocyanate, or 4,4'-diphenylmethane diisocyanate and hydrogenated methylene diisocyanate (HMDI). Other exemplary isocyanates include hexamethylene diisocyanate and other toluene diisocyanates such as 2,4-toluene diisocyanate and 2,6-toluene diisocyanate, 4,4' tolidine diisocyanate, m-phenylene diisocyanate, 4-chloro-1,3-phenylene diisocyanate, 4,4-tetramethylene diisocyanate, 1,6-hexamethylene diisocyanate, 1,10-decamethylene diisocyanate, 1,4-cyclohexylene diisocyanate, 4,4'-methylene bis(cyclohexylisocyanate), 1,4-isophorone diisocyanate, 3,3'-dimethyl-4,4'-diphenylmethane diisocyanate, 1,5-tetrahydronaphthalene diisocyanate, and mixtures of such diisocyanates. Also included among the isocyanates applicable to this invention are specialty isocyanates containing sulfonated groups for improved hemocompatibility and the like.

Suitable chain extenders included in this polymerization of the polycarbonate urethanes should have a functionality that is equal to or greater than two. A preferred and well-recognized chain extender is 1,4-butanediol. Generally speaking, most diols or diamines are suitable, including the ethylenediols, the propylenediols, ethylenediamine, 1,4-butanediamine methylene dianiline heteromolecules such as ethanolamine, reaction products of said diisocyanates with water and combinations of the above.

The polycarbonate urethane polymers according to the present invention should be substantially devoid of any significant ether linkages (i.e., when y is 0, 1 or 2 as represented in the general formula hereinabove for a polycarbonate macroglycol), and it is believed that ether linkages should not be present at levels in excess of impurity or side reaction concentrations. While not wishing to be bound by any specific theory, it is presently believed that ether linkages account for much of the degradation that is experienced by polymers not in accordance with the present invention due to enzymes that are typically encountered in vivo, or otherwise, attack the ether linkage via oxidation. Live cells probably catalyze degradation of polymers containing linkages. The polycarbonate urethanes useful in the present invention avoid this problem.

Because minimal quantities of ether linkages are unavoidable in the polycarbonate producing reaction, and because these ether linkages are suspect in the biodegradation of polyurethanes, the quantity of macroglycol should be minimized to thereby reduce the number of ether linkages in the polycarbonate urethane. In order to maintain the total number of equivalents of hydroxyl terminal groups approximately equal to the total number of equivalents of isocyanate terminal groups, minimizing the polycarbonate soft segment necessitates proportionally increasing the chain extender hard segment in the three component polyurethane system. Therefore, the ratio of equivalents of chain extender to macroglycol should be as high as possible. A consequence of increasing this ratio (i.e., increasing the amount of chain extender with respect to macroglycol) is an increase in hardness of the polyurethane. Typically, polycarbonate urethanes of hardnesses, measured on the Shore scale, less than 70A show small amounts of biodegradation. Polycarbonate urethanes of Shore 75A and greater show virtually no biodegradation.

The ratio of equivalents of chain extender to polycarbonate and the resultant hardness is a complex function that includes the chemical nature of the components of the urethane system and their relative proportions. However, in general, the hardness is a function of the molecular weight of both chain extender segment and polycarbonate segment and the ratio of equivalents thereof. Typically, the 4,4'-methylene bisphenyl diisocyanate (MDI) based systems, a 1,4-butanediol chain extender of molecular weight 90 and a polycarbonate urethane of molecular weight of approximately 2000 will require a ratio of equivalents of at least about 1.5 to 1 and no greater than about 12 to 1 to provide non-biodegrading polymers. Preferably, the ratio should be at least about 2 to 1 and less than about 6 to 1. For a similar system using a polycarbonate glycol segment of molecular weight of about 1000, the preferred ration should be at least about 1 to 1 and no greater than about 3 to 1. A polycarbonate glycol having a molecular weight of about 500 would require a ratio in the range of about 1.2 to about 1.5:1.

The lower range of the preferred ratio of chain extender to macroglycol typically yields polyurethanes of Shore 80A hardness. The upper range of ratios typically yields polycarbonate urethanes on the order of Shore 75D. The preferred elastomeric and biostable polycarbonate urethanes for most medical devices would have a Shore hardness of approximately 85A.

Generally speaking, it is desirable to control somewhat the cross-linking that occurs during polymerization of the polycarbonate urethane polymer. A polymerized molecular weight of between about 80,000 and about 200,000 Daltons, for example on the order of about 120,000 Daltons (such molecular weights being determined by measurement according to the polystyrene standard), is desired so that the resultant polymer will have a viscosity at a solids content of 43% of between about 900,000 and about 1,800,000 centipoise, typically on the order of about 1,000,000 centipoise. Cross-linking can be controlled by avoiding an isocyanate-rich situation. Of course, the general relationship between the isocyanate groups and the total hydroxyl (and/or amine) groups of the reactants should be on the order of approximately 1 to 1. Cross-linking can be controlled by controlling the reaction temperatures and shading the molar ratios in a direction to be certain that the reactant charge is not isocyanate-rich; alternatively a termination reactant such as ethanol can be included in order to block excess isocyanate groups which could result in cross-linking which is greater than desired.

Concerning the preparation of the polycarbonate urethane polymers, they can be reacted in a single-stage reactant charge, or they can be reacted in multiple states, preferably in two stages, with or without a catalyst and heat. Other components such as antioxidants, extrusion agents and the like can be included, although typically there would be a tendency and preference to exclude such additional components when a medical-grade polymer is being prepared.

Additionally, the polycarbonate urethane polymers can be polymerized in suitable solvents, typically polar organic solvents in order to ensure a complete and homogeneous reaction. Solvents include dimethylacetamide, dimethylformamide, dimethylsulfoxide toluene, xylene, m-pyrrol, tetrahydrofuran, cyclohexanone, 2-pyrrolidone, and the like, or combinations thereof. These solvents can also be used to delivery the polymers to the ePTFE layer of the present invention.

A particularly desirable polycarbonate urethane is the reaction product of polyhexamethylenecarbonate diol, with methylene bisphenyl diisocyanate and the chain extender 1,4-butanediol.

The use of the elastomeric bonding agent in solution is particularly beneficial in that by coating the surface 19 of ePFTE layer 14, the bonding agent solution enters the pores 18 of layer 14 defined by the IND of the ePTFE layer. As the ePTFE is a highly hydrophobic material, it is difficult to apply a bonding agent directly to the surface thereof. By providing a bonding agent which may be disposed within the micropores of the ePFTE structure, enhanced bonding attachment between the bonding agent and the ePFTE surface is achieved.

The bonding agents of the present invention, particularly the materials noted above and, more particularly, polycarbonate urethanes, such as those formed from the reaction of alphatic macroglycols and aromatic or aliphatic diisocyanates, are elastomeric materials which exhibit elastic properties. Conventional ePTFE is generally regarded as an inelastic material, i.e., even though it can be further stretched, it has little memory. Therefore, conventional ePTFE exhibits a relatively low degree of longitudinal compliance. Also, suture holes placed in conventional ePTFE structures do not self-seal, due to the inelasticity of the ePTFE material. By applying an elastomeric coating to the ePTFE structure, both longitudinal compliance and suture hole sealing are enhanced.

Referring again to FIG. 1, textile layer 12 is secured to surface 19 of ePFTE layer 14 which has been coated with bonding agent 20. The textile layer 12 is secured by placing it in contact with the bonding agent. As it will be described in further detail hereinbelow, this process can be performed either by mechanical, chemical, or thermal techniques or combinations thereof.

The composite prosthesis 10 may be used in various vascular applications in planar form as a vascular patch or in tubular form as a graft. The textile surface may be designed as a tissue contacting surface in order to promote enhanced cellular ingrowth which contributes to the long term patency of the prosthesis. The ePTFE surface 14 may be used as a blood contacting surface so as to minimize leakage and to provide a generally anti-thrombogetic surface. While this is the preferred usage of the composite prosthesis of the prevent invention, in certain situations, the layers may be reversed where indicated.

The present invention provides for various embodiments of composite ePTFE/textile prosthesis.

The composite ePTFE-lined textile graft is desirably formed as follows. A thin ePFTE tube is formed in a conventional forming process such as by tubular extrusion or by sheet extrusion where the sheet is formed into a tubular configuration. The ePTFE tube is placed over a stainless steel mandrel and the ends of the tube are secured. The ePTFE tube is then spray coated with an adhesive solution of anywhere from 1%-15% Corethane® urethane, 2.5 W30 in DMAc. As noted above, other adhesive solutions may also be employed. The coated ePTFE tube is placed in an oven heated in a range from 18° C. to 150° C. oven for 5 minutes to overnight to dry off the solution. If desired, the spray coating and drying process can be repeated multiple times to add more adhesive to the ePTFE tube. The coated ePTFE tube is then covered with the textile tube to form the composite prosthesis. One or more layers of elastic tubing, preferably silicone, is then placed over the composite structure. This holds the composite structure together and assures that complete contact and adequate pressure is maintained for bonding purposes. The assembly of the composite graft within the elastic tubing is placed in an oven and heated in a range of 180°-220° C. for approximately 5-30 minutes to bond the layers together.

Thereafter, the ePTFE lined textile graft may be crimped along the tubular surface thereof to impart longitudinal compliance, kink resistance and enhanced handling characteristics. The crimp may be provided by placing a coil of metal or plastic wire around a stainless steel mandrel. The graft is slid over the mandrel and the coil wire. Another coil is wrapped around the assembly over the graft to fit between the spaces of the inner coil. The assembly is then heat set and results in the formation of the desired crimp pattern. It is further contemplated that other conventional crimping processes may also be used to impart a crimp to the ePTFE textile graft.

In order to further enhance the crush and kink resistance of the graft, the graft can be wrapped with a polypropylene monofilament. This monofilament is wrapped in a helical configuration and adhered to the outer surface of the graft either by partially melting the monofilament to the graft or by use of an adhesive.

The ePTFE-lined textile graft exhibits advantages over conventional textile grafts in that the ePTFE liner acts as a barrier membrane which results in less incidences of bleeding without the need to coat the textile graft in collagen. The wall thickness of the composite structure may be reduced while still maintaining the handling characteristics, especially where the graft is crimped. A reduction in suture hole bleeding is seen in that the elastic bonding agent used to bond the textile to the ePTFE, renders the ePTFE liner self-sealing.

The process for forming the textile covered ePTFE vascular graft may be described as follows.

An ePTFE tube formed preferably by tubular paste extrusion is placed over a stainless steel mandrel. The ends of the ePTFE tube are secured. The ePTFE tube is coated using an adhesive solution of from 1%-15% Corethane®, 2.5 W30 and DMAc. The coated ePTFE tubular structure is then placed in an oven heated in a range from 18° C. to 150° C. for 5 minutes to overnight to dry off the solution. The coating and drying process can be repeated multiple times to add more adhesive to the ePTFE tubular structure.

Once dried, the ePTFE tubular structure may be longitudinally compressed in the axial direction to between 1% to 85% of its length to relax the fibrils of the ePTFE. The amount of desired compression may depend upon the amount of longitudinal expansion that was imparted to the base PTFE green tube to create the ePTFE tube. Longitudinal expansion and compression may be balanced to achieve the desired properties. This is done to enhance the longitudinal stretch properties of the resultant graft. The longitudinal compression process can be performed either by manual compression or by thermal compression.

The compressed ePTFE tube is then covered with a thin layer of the textile tube. One or more layers of elastic tubing, preferably silicone, is placed over the composite. This holds the composite together and assures that there is complete contact and adequate pressure. The assembly is then placed in a 205° C. oven for approximately 10-20 minutes to bond the layers together.

The composite graft can be wrapped with a polypropylene monofilament which is adhered to the outer surface by melting or use of an adhesive. The polypropylene monofilament will increase the crush and kink resistance of the graft. Again, the graft can be crimped in a convention manner to yield a crimped graft.

The textile covered ePTFE graft exhibits superior longitudinal strength as compared with conventional ePTFE vascular grafts. The composite structure maintains high suture retention strength and reduced suture hole bleeding. This is especially beneficial when used as a dialysis access graft in that the composite structure has increased strength and reduced puncture bleeding. This is achieved primarily by the use of an elastomeric bonding agent between the textile tubular structure and the ePTFE tubular structure in which the elastic bonding agent has a tendency to self-seal suture holes.

As is well known, the vascular patch may be used to seal an incision in the vascular wall or otherwise repair a soft tissue area in the body. The ePTFE surface of the vascular patch would be desirably used as the blood contacting side of the patch. This would provide a smooth luminal surface and would reduce thrombus formation. The textile surface is desirably opposed to the blood contacting surface so as to promote cellular ingrowth and healing.

The composite vascular patch may be formed by applying the bonding agent as above described to one surface of the ePTFE layer. Thereafter, the textile layer would be applied to the coated layer of ePTFE. The composite may be bonded by the application of heat and pressure to form the composite structure. The composite vascular patch of the present invention exhibits many of the above stated benefits of using ePTFE in combination with a textile material. The patches of the present invention may also be formed by first making a tubular construction and then cutting the requisite planar shape therefrom.

Figure 2:
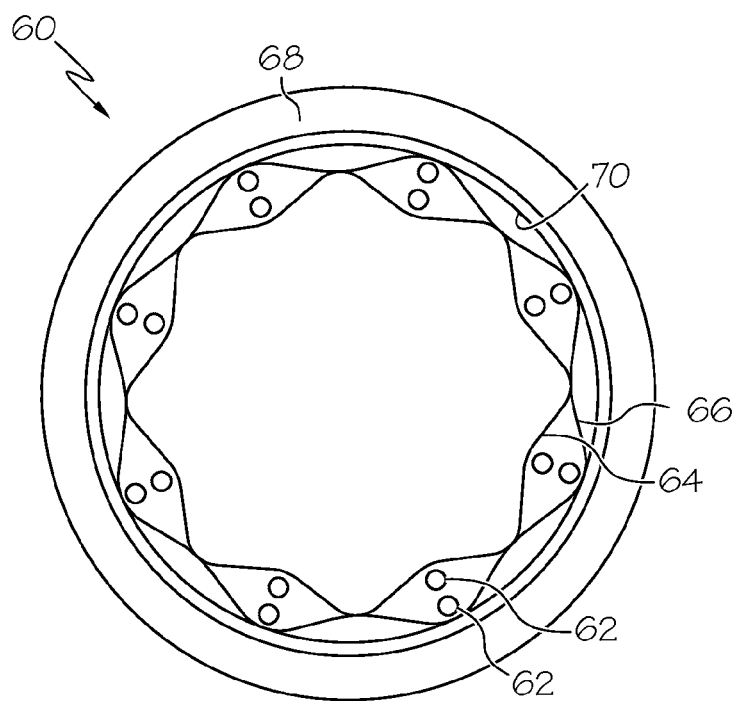
FIGS. 2 and 3 show a schematic cross-section of preferred embodiments of the present invention.
Figure 3:
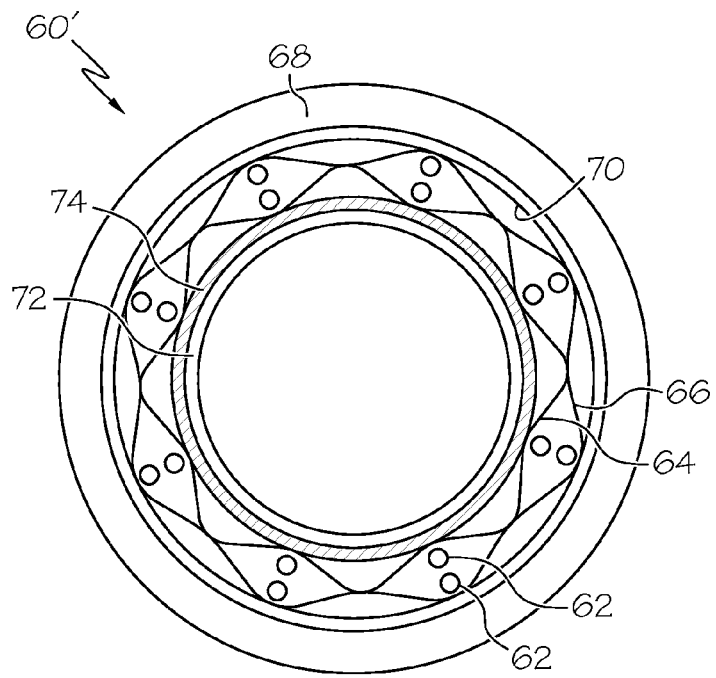

With reference to FIGS. 2 and 3, various embodiments of a multi-layered composite graft are depicted. With reference to FIG. 2, a composite graft 60 is shown having a tubular support structure 62 interposed between inner and outer ePTFE layers 64 and 66. The ePTFE layers 64 and 66 are joined using any technique known to those skilled in the art, such as by sintering or with an adhesive (thermoplastic fluoropolymer adhesive (FEP)). The ePTFE layers 64, 66 are joined through interstices found in the support structure 62, preferably without being affixed to the support structure 62. The outer ePTFE layer 66 is bonded to a textile layer 68 with a layer of bonding agent 70. The arrangement of the layers may be altered, wherein the support structure 62 and the ePTFE layers 64, 66 may be disposed externally of the textile layer 68 with the layer of bonding agent 70 being interposed between the textile layer 68 and the inner ePTFE layer 64. The composite graft is formed to allow for simultaneous radial expansion of the support structure 62 along with the ePTFE layers 64, 66 and the textile layer 68. The radial expansion is preferably unhindered by any of the constituent elements of the composite graft.

Figure 5:
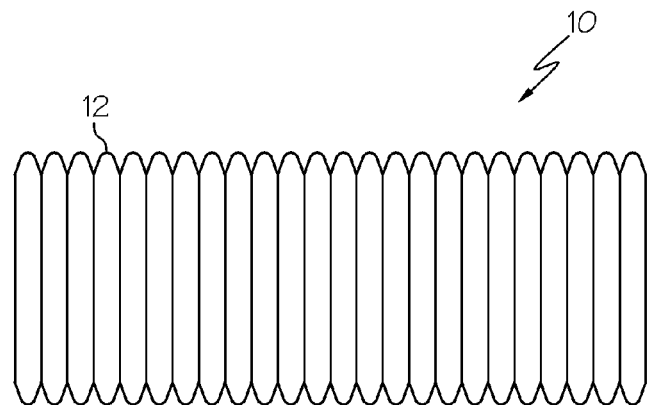
FIG. 5 is a perspective view of a textile graft having a plurality of longitudinally spaced crimps therealong.
Figure 6:
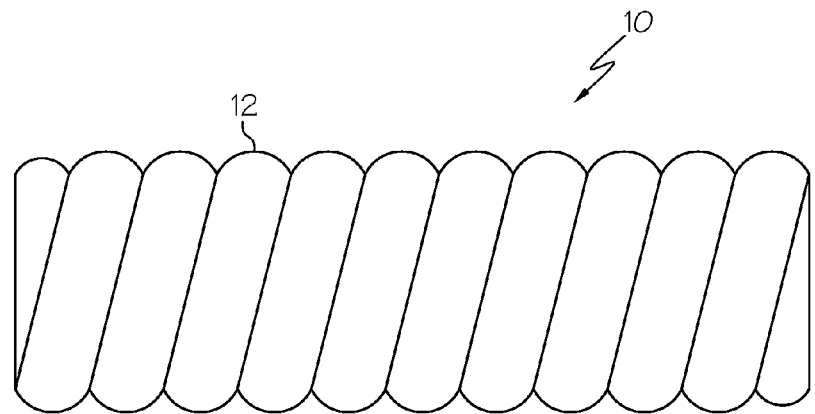
FIG. 6 is a perspective view of a textile graft having helically wrapped monofilament externally therearound.

FIG. 5 presents a perspective drawing which shows a textile graft having a plurality of longitudinally spaced crimps therealong. FIG. 6 shows the textile graft helically wrapped with a monofilament externally therearound.

The tubular support structure 62 may be any structure known in the art which is capable of maintaining patency of the composite graft 60 in a bodily vessel. For example, the support structure 62 may be a stent, and preferably is radially-expandable. Radially-expandable member 62 may be of any stent configuration known to those skilled in the art, including those used alone or in a stent/graft arrangement. Various stent types and stent constructions may be employed in the present invention including, without limitation, self-expanding stents and balloon expandable stents. The stents may be capable of radially contracting as well. Self-expanding stents include those that have a spring-like action which cause the stent to radially expand or stents which expand due to the memory properties of the stent material for a particular configuration at a certain temperature. Nitinol® is an example of a material which may be used as a self-expanding stent. Other materials are of course contemplated, such as stainless steel, platinum, gold, titanium, tantalum, niobium, and other biocompatible materials, as well as polymeric stents. The configuration of the stent may also be chosen from a host of geometries. For example, wire stents can be fastened in a continuous helical pattern, with or without wavelike forms or zigzags in the wire, to form a radially deformable stent. Individual rings or circular members can be linked together such as by struts, sutures, or interlacing or locking of the rings to form a tubular stent. Although a wide variety of distensible members may be used, FIG. 2 shows one particular distensible member 62, a stent, which may be employed in prosthesis 60. The particular stent shown in FIG. 2 is more fully described in commonly assigned U.S. Pat. No. 5,693,085 to Buirge et al. and the disclosure of U.S. Pat. No. 5,693,085 is incorporated by reference herein.

With reference to FIG. 3, an alternative embodiment of the composite graft 60 is shown therein and designated generally with the reference numeral 60'. Like numbers are used to designate like elements. With this embodiment, an additional inner textile reinforcement 72 is provided which is fixed by an inner layer of bonding agent 74.

The textile layers 68, 72 and the bonding agent layers 70, 74 may be of any structure described in the embodiments above. Likewise, the interaction between the ePTFE layers, the textile layers, and the bonding agent 70, 74 is the same interaction described above.

With either embodiment of the composite graft 60, 60', an implantable prosthesis may be formed which is self-supporting and usable to maintain patency of a bodily vessel, such as in the coronary vasculature, esophagus, trachea, colon, biliary tract, urinary tract, prostate, and brain. Also, the composite graft 60, 60' may be treated with any of the following: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, antithrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

Figure 4:
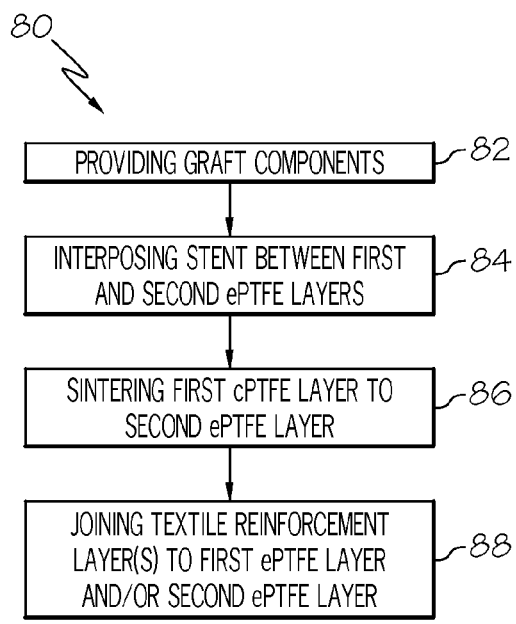
FIG. 4 is a flow chart exemplifying a process for preparing one of the structures of FIGS. 2 and 3.

In an exemplary method of forming the composite graft 60, 60', flow chart 80 is presented in FIG. 4. In an initial step 82, components of the composite graft 60, 60' are provided, including the support structure 62; the inner and outer ePTFE layers 64, 66; the textile reinforcement 68 (and, optionally, inner textile reinforcement layer 72); and, bonding agent to form layers 70 and/or 74. Thereafter, the support structure 62 is interposed between the first and second ePTFE layers 64, 66, for example, on a mandrel. The ePTFE layers 64 and 66 are sintered together so as to bond through the interstices of the support structure 62. The textile layer 68, and, optionally, the textile reinforcement 72, are joined using the layers of bonding agents 70 and 74 in the same process described above with previous embodiments (step 88).

Various changes to the foregoing described and shown structures will now be evident to those skilled in the art. Accordingly, the particularly disclosed scope of the invention is set forth in the following claims.

What is claimed is:

1. A composite multilayer implantable structure comprising:
   a first inner tubular layer and second outer tubular layer formed of expanded polytetrafluoroethyene having a porous microstructure defined by nodes interconnected by fibrils, said first and second layers each seamless and substantially fluid-tight, said first and second layers each formed from a green fluoropolymer tube characterized by a generally uniform thickness being in the range of up to about 250 µm, said first and second layers having a support structure positioned there between, wherein said first layer is a blood contacting layer;
   a third tubular layer formed of textile material circumferentially disposed exteriorly to said first and second layers, wherein said third tubular layer is a tissue contacting layer; and
   an elastomeric bonding agent layer with a Shore Hardness of about 75 to 85A, said layer consisting essentially of a material selected from the group consisting of polycarbonate urethanes, styrene-isobutylene block copolymers, and combinations thereof, applied to cover one of said second layer or third layer and disposed within the pores of said microstructure to seal punctures, and for securing said second layer to said third layer;
   wherein said first, second, and third tubular layers form an elongate vascular graft.

2. A composite structure of claim 1 wherein said bonding agent is applied to one surface of said second layer.

3. A composite structure of claim 2 wherein said third layer is placed in contact with said one surface of said second layer.

4. A composite structure of claim 1 wherein said bonding agent is applied to a surface of said third textile layer.

5. A composite structure of claim 1 wherein said third layer comprises a textile pattern selected from the group comprising knits, weaves, stretch-knits, braids, any non-woven process, and combinations thereof.

6. A composite structure of claim 1 wherein said support structure comprises a stent.

7. A composite structure of claim 1 wherein said graft includes a plurality of longitudinally spaced crimps therealong.

8. A composite structure of claim 1 wherein said graft is helically wrapped with a monofilament externally therearound.

9. A composite structure of claim 8 wherein said monofilament comprises polypropylene.

10. A composite structure of claim 9 wherein said monofilament is attached by heat bonding.

11. A composite structure of claim 8 wherein said graft includes an external support coil helically positioned thereover.

12. A composite structure of claim 1 wherein said elastomeric bonding agent is applied to said second layer in solution.

13. A composite structure of claim 12 wherein said solution includes dimethylacetamide.

14. A composite structure of claim 1 further comprising a fourth tubular layer formed of textile material circumferentially disposed interiorly to said first and second layers; and an elastomeric bonding agent applied to one of said first layer or said fourth layer and disposed within the pores of said microstructure for securing said first layer to said fourth layer.

15. A composite structure of claim 1, wherein the first inner tubular layer and the second outer tubular layer are each a discrete tubular layer.

* * * * *